United States Patent [19]
Kushida et al.

[11] Patent Number: 5,928,910
[45] Date of Patent: Jul. 27, 1999

[54] ANTIFUNGAL SUBSTANCES BE-49385 AND PROCESS FOR THEIR PRODUCTION

[75] Inventors: Hiroshi Kushida; Shigeru Nakajima; Shigeru Uchiyama; Masao Nagashima; Katsuhisa Kojiri; Kenji Kawamura; Hiroyuki Suda, all of Isukuba, Japan

[73] Assignee: Banyu Pharmaceutical Co., Ltd., Tokyo, Japan

[21] Appl. No.: 09/068,556

[22] PCT Filed: Nov. 15, 1996

[86] PCT No.: PCT/JP96/03354

§ 371 Date: May 19, 1998

§ 102(e) Date: May 19, 1998

[87] PCT Pub. No.: WO97/19186

PCT Pub. Date: May 29, 1997

[30] Foreign Application Priority Data

Nov. 21, 1995 [JP] Japan ..................................... 7-326487
Apr. 9, 1996 [JP] Japan ..................................... 8-111901

[51] Int. Cl.$^6$ ........................ A61K 31/35; C07D 311/78; C12P 15/00; C12P 17/06
[52] U.S. Cl. ........................ 435/125; 435/127; 435/170; 514/453; 549/276
[58] Field of Search ..................................... 435/125, 127, 435/170; 514/453; 549/276

[56] References Cited

U.S. PATENT DOCUMENTS 5,233,062 8/1993 Horn et al. .

OTHER PUBLICATIONS

Sutterlin et al. EMBO, vol. 16 211, pp. 6374–6383, 1997.

Primary Examiner—Johann Richter
Assistant Examiner—Taofiq A. Solola
Attorney, Agent, or Firm—Oblon, Spivak, McClelland, Maier & Neustadt, P.C.

[57] ABSTRACT

The present invention relates to a compound represented by the general formula (I):

(I)

wherein $R_1$ is a hydrogen atom, or and $R_2$ is a hydrogen atom or OH and $R_2$ is a hydrogen atom or a lower alkanoyl group, and an antifungal agent containing it as an active ingredient.

15 Claims, No Drawings

ANTIFUNGAL SUBSTANCES BE-49385 AND PROCESS FOR THEIR PRODUCTION

TECHNICAL FIELD

The present invention is useful in the pharmaceutical field. More specifically, the present invention relates to novel compounds which provide antifungal effects, a process for their production and applications thereof, and a microorganism which produces such compounds.

BACKGROUND ART

In the field of chemotherapy against microbism, many compounds have already been practically used as pharmaceutical products. However, existing chemotherapic agents are not necessarily adequate in their effects against mycosis due to infection of so-called eumycetes such as fungi or yeast, and emergence of resistant strains has become a serious clinical problem.

DISCLOSURE OF THE INVENTION

It is an object of the present invention to find out a novel antifungal agent having stronger antifungal activities against fungi.

The present inventors have conducted screening of secondary metabolites of microorganisms widely with respect to the substances having antifungal activities to accomplish the object, and as a result, have found that the compound represented by the after-mentioned general formula (I) has excellent antifungal activities, and the present invention has been accomplished.

Namely, the present invention provides a novel compound represented by the general formula (I):

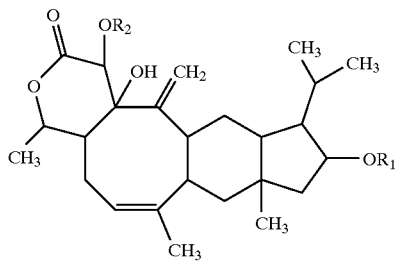

(I)

wherein $R_1$ is a hydrogen atom, or

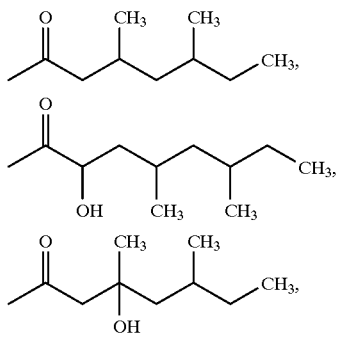

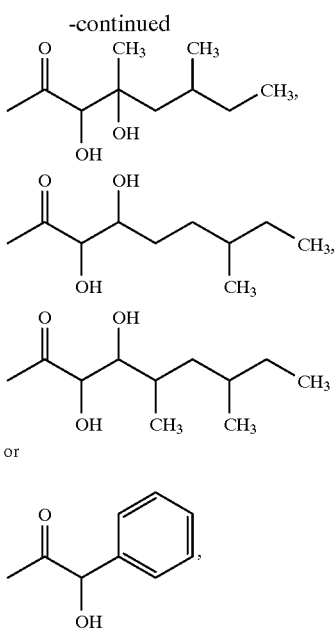

and $R_2$ is a hydrogen atom or a lower alkanoyl group; a process for its production and its application, and a microorganism belonging to genus Paecilomyces, which is capable of producing a compound represented by the general formula (II):

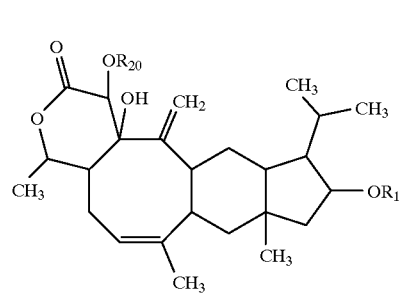

(II)

wherein $R_{20}$ is a hydrogen atom, and $R_1$ is as defined above.

Among the compounds of the general formula (I) of the present invention, a compound wherein $R_1$ is a group represented by

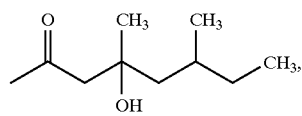

and $R_2$ is a hydrogen atom, will be referred to as BE-49385A, a compound wherein $R_1$ is a group represented by

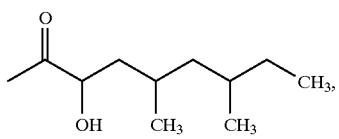

and $R_2$ is a hydrogen atom, will be referred to as BE-49385B, a compound wherein $R_1$ is a group represented by

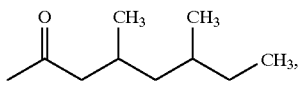

and $R_2$ is a hydrogen atom, will be referred to as BE-49385C, a compound wherein $R_1$ is a group represented by

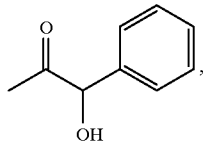

and $R_2$ is a hydrogen atom, will be referred to as BE-49385D, a compound wherein $R_1$ is a group represented by

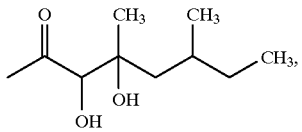

and $R_2$ is a hydrogen atom, will be referred to as BE-49385E, a compound wherein each of $R_1$ and $R_2$ is a hydrogen atom, will be referred to as BE-49385F, a compound wherein $R_1$ is a group represented by

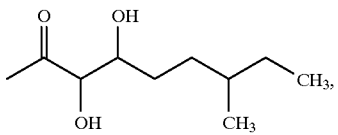

and $R_2$ is a hydrogen atom, will be referred to as BE-49385G, a compound wherein $R_1$ is a group represented by

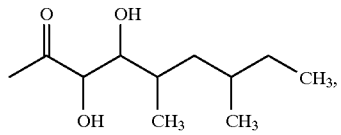

and $R_2$ is a hydrogen atom, will be referred to as BE-49385H, and a compound wherein $R_1$ is a group represented by

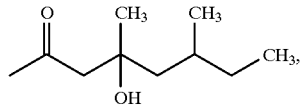

and $R_2$ is an acetyl group, will be referred to as BE-49385A-Ac.

The term "lower" used in the present specification means that the carbon number of the group having this term affixed, is at most 6, preferably at most 4. The "lower alkanoyl group" means a $C_{1-6}$ linear or branched alkanoyl group, such as, a formyl group, an acetyl group, a propionyl group, an isopropionyl group, an isobutyryl group, a sec-butyryl group, a tert-butyryl group, a pentanoyl group, an isopentanoyl group, a neopentanoyl group or a hexanoyl group.

Now, the physicochemical characteristics of the antifungal substances BE-49385 of the present invention will be shown. The abbreviations in the NMR measurements have the following meanings.

s: singlet
d: doublet
t: triplet
q: quartet
m: multiplet
br: broad
J: coupling constant
Hz: hertz Physicochemical characteristics of BE-49385A
Nature: White amorphous solid or crystals
Molecular formula: $C_{34}H_{54}O_7$
Mass spectrometry: [High resolution FAB-MS] as (M+H):
measured value 575.3945,
calculated value 575.3947
Specific rotation:$[\alpha]_D^{20}$=−66.0° (c=1.00, $CHCl_3$)
Ultraviolet absorption spectrum: Terminal absorption is shown.
Infrared absorption spectrum: (KBr, $cm^{-1}$):
3496, 3438, 3398, 2962, 1727, 1540, 1459, 1382, 1197, 1135
$^1$H-NMR spectrum (500MHz, $CDCl_3$) δ ppm:
5.30(1H, dt, J=7.3, 4.0 Hz), 5.14(1H, s), 5.04(1H, brt, J=9.0 Hz), 4.71(1H, s), 4.38(1H, dq, J=10.0, 6.4H z), 4.22 (1H, d, J=4.0 Hz), 3.58(1H, s), 3.12(2H, m), 3.07 (1H, d, J=4.0 Hz), 2.80(1H, s), 2.49(1H, d, J=15.6H z), 2.39(1H, d, 15.6Hz), 2.26(1H, dd, J=11.6, 7.3Hz), 2.20(1H, brt, J=12.2Hz), 1.92–2.07(4H, m), 1.66–1.85(3 H, m), 1.63(3H, s), 1.54(2H, m), 1.46(3H, d, J=6.4H z), 1.31–1.43(3H, m), 1.23(3H, s), 1.13–1.26(2H, m), 1.08 (1H, t, J=12.2Hz), 0.98(3H, s), 0.94(6H, d, J=6.4H z), 0.90(3H, d, J=6.4Hz), 0.87(3H, t, J=7.0 Hz)
$^{13}$C-NMR spectrum (125 MHz, $CDCl_3$) δ ppm:
173.0(s), 172.7(s), 150.4(s), 143.0(s), 116.7(d), 110.9(t), 79.8(d), 77.5(d), 76.4(s), 74.5(d), 71.5(s), 53.3 (d), 50.5(d), 49.4(d), 48.2(t), 47.3(t), 45.8(t), 45.7 (d), 45.6(t), 43.3(d), 42.2(s), 35.0(t), 31.0(t), 30.3 (d), 29.6(d), 27.2(q), 26.2(q), 23.9(q), 21.7(q), 21.5 (t), 21.3(q), 20.5(q), 19.4(q); 11.2(q)
Solubility: Readily soluble in an organic solvent such as methanol or dimethylsulfoxide, and hardly soluble in water.
Distinction of acidic, neutral or basic substance:
Neutral substance
Color reaction: Sulfuric acid reaction positive,
Phosphorus molybdate reaction positive
$R_f$ value: 0.29 (using Kieselgel $60F_{254}$, manufactured by Merck Co., developing solvent:
toluene/tetrahydrofuran/methanol (50:10:1))
Physicochemical characteristics of BE-49385B
Nature: White amorphous solid or crystals
Molecular formula: $C_{35}H_{56}O_7$
Mass spectrometry: [High resolution FAB-MS] as $(M+H)^+$:
measured value 589.4083,
calculated value 589.4104
Ultraviolet absorption spectrum: Terminal absorption is shown.
$^1$H-NMR spectrum (500MHz, $CDCl_3$) δ ppm:
5.33(1H, dt, J=7.3, 4.0 Hz), 5.14(1H, s), 5.04(1H, brt, J=9.2 Hz), 4.71(1H, s), 4.38(1H, dq, J=11.0, 6.3H z), 4.22

(1H, s), 4.16(1H, m), 3.06–3.16(3H, m), 2.83 (1H, s), 2.65(1H, d, J=6.1 Hz), 2.24(1H, dd, J=11.6, 7. 3 Hz), 2.20(1H, m), 2.05(2H, m), 1.96(2H, m), 1.81(3H, m), 1.71 (1H, m), 1.67(1H, m), 1.63(3H, s), 1.46(3H, d, J=6.3Hz), 1.25–1.46(5H, m), 1.15(1H, dd, J=11.6, 7.3 Hz), 1.08(2H, m), 0.98(3H, s), 0.95(1H, m), 0.94(3H, d, J=6.4 Hz), 0.93 (3H, d, J=6.7 Hz), 0.89(3H, d, J=6.4 Hz), 0.87(3H, d, J=6.4 Hz), 0.86(3H, t, J=7.0 Hz)

$^{13}$C-NMR spectrum (125 MHz, CDCl$_3$) δ ppm:
175.3(s), 173.0(s), 150.4(s), 142.9(s), 116.7(d), 110.9 (t), 80.8(d), 77.5(d), 76.4(s), 74.4(d), 69.0(d), 53.2 (d), 50.5(d), 49.4(d), 47.1(t), 45.7(t), 45.7(d), 43.9(t), 43.3(d), 42.3(t), 42.3(s), 34.9(t), 31.4(d), 29.5(d), 28.5 (t), 26.8(d), 26.2(q), 23.9(q), 21.6(q), 21.5(t), 20.6 (q), 20.4(q), 19.9(q), 19.4(q), 10.9(q)

Solubility: Readily soluble in an organic solvent such as methanol or dimethylsulfoxide, and hardly soluble in water.
Distinction of acidic, neutral or basic substance:
Neutral substance
Color reaction: Sulfuric acid reaction positive,
Phosphorus molybdate reaction positive
$R_f$ value: 0.30 (using Kieselgel 60F$_{254}$, manufactured by Merck Co., developing solvent:
toluene/tetrahydrofuran/methanol (50:10:1))

Physicochemical characteristics of BE-49385C
Nature: White amorphous solid or crystals
Molecular formula: $C_{34}H_{54}O_6$
Mass spectrometry: [High resolution FAB-MS] as (M+H)$^+$:
measured value 559.3984,
calculated value 559.3999
Ultraviolet absorption spectrum: Terminal absorption is shown.

$^1$H-NMR spectrum (500MHz, CDCl$_3$) δ ppm:
5.23(1H, dt, J=7.6, 4.0 Hz), 5.14(1H, s), 5.04(1H, brt, J=9.0 Hz), 4.71(1H, s), 4.38(1H, dq, J=11.0, 6.4H z), 4.21 (1H, brs), 3.05–3.16(3H, m), 2.84(1H, s), 2.16–2.27(3H, m), 1.90–2.07(6H, m), 1.82(1H, dt, J=12.8, 2.8 Hz), 1.67–1.78 (2H, m), 1.63(3H, s), 1.46(3H, d, J=6.4 Hz), 1.32–1.43(3H, m), 1.23(1H, m), 1.04–1.16(3H, m), 0.99(1H, m), 0.97(3H, s), 0.93(3H, d, J=6.4Hz), 0.91 (3H, d, J=6.4Hz), 0.88(3H, d, J=6.4Hz), 0.86(3H, d, J=6.4Hz), 0.86(3H, t, J=7.3Hz)

$^{13}$C-NMR spectrum (125MHz, CDCl$_3$) δ ppm:
173.0(s), 172.8(s), 150.5(s), 143.1 (s), 116.6(d), 110.9 (t), 79.1 (d), 77.5 (d), 76.4 (s), 74.5 (d), 53.3 (d), 50.5 (d), 49.4(d), 47.3(t), 45.8(t), 45.8(d), 44.1(t), 43.4(d), 42.2(s), 42.1(t), 35.1(t), 29.7(d), 29.0(t), 28.0(d), 26.2 (q), 23.9(q), 21.7(q), 21.5(t), 20.4(q), 20.2(q), 19.5 (q), 19.4(q), 11.0 (q)

Solubility: Readily soluble in an organic solvent such as methanol or dimethylsulfoxide, and hardly soluble in water.
Distinction of acidic, neutral or basic substance:
Neutral substance
Color reaction: Sulfuric acid reaction positive,
Phosphorus molybdate reaction positive
$R_f$ value: 0.43 (using Kieselgel 60F$_{254}$, manufactured by Merck Co., developing solvent:
toluene/tetrahydrofuran/methanol (50:10:1))

Physicochemical characteristics of BE-49385D
Nature: White amorphous solid or crystals
Molecular formula: $C_{33}H_{44}O_7$
Mass spectrometry: [High resolution FAB-MS] as (M+H)$^+$:
measured value 553.3180,
calculated value 553.3165
Ultraviolet absorption spectrum: Terminal absorption is shown.

$^1$H-NMR spectrum (500MHz, CDCl$_3$) δ ppm:
7.30–7.41(5H, m), 5.32(1H, dt, J=7.3, 4.0 Hz), 5.12 (2H, brs), 5.01 (1H, t, J=9.0 Hz), 4.70(1H, s), 4.36(1H, dq, J=11.0, 6.4 Hz), 4.20(1H, s), 3.44(1H, d, J=5.8 Hz), 3.00–3.12(3H, m), 2.77(1H, s), 2.16(1H, dt, J=12.5, 3.1 Hz), 2.10(1H, dd, J=12.0, 7.3 Hz), 2.03(1H, dd, J=11.0, 6.4 Hz), 1.93(2H, m), 1.88(1H, dd, J=12.5, 3.1 Hz), 1.77(2H, m), 1.69(1H, m), 1.60(3H, s), 1.45(3H, d, J=6.4 Hz), 1.34(1H, ddd, J=12.5, 12.5, 12.5 Hz), 0.95(1 H, m), 0.94(3H, s), 0.93(3H, d, J=6.3 Hz), 0.90(3H, d, J=6.3 Hz), 0.86(1H, m)

$^{13}$C-NMR spectrum (125MHz, CDCl$_3$) δ ppm:
173.1 (s), 172.9(s), 150.4(s), 142.7(s), 138.3(s), 128.4(d), 128.4(d), 128.3(d), 126.4(d), 126.4(d), 116.7(d), 110.9(t), 81.5(d), 77.5(d), 76.3(s), 74.4(d), 72.8(d), 53.1(d), 50.3(d), 49.4(d), 46.4(t), 45.6(d), 45.6(t), 43.2 (d), 42.1(s), 34.9(t), 29.5(d), 26.2(q), 23.9(q), 21.6(q), 21.5(t), 20.4(q), 19.4(q)

Solubility: Readily soluble in an organic solvent such as methanol or dimethylsulfoxide, and hardly soluble in water.
Distinction of acidic, neutral or basic substance:
Neutral substance
Color reaction: Sulfuric acid reaction positive,
Phosphorus molybdate reaction positive
$R_f$ value: 0.19 (using Kieselgel 60F$_{254}$, manufactured by Merck Co., developing solvent:
toluene/tetrahydrofuran/methanol (50:10:1))

Physicochemical characteristics of BE-49385E
Nature: White amorphous solid or crystals
Molecular formula: $C_{34}H_{54}O_8$
Mass spectrometry: [High resolution FAB-MS] as (M+H)$^+$:
measured value 591.3880,
calculated value 591.3897
Ultraviolet absorption spectrum: Terminal absorption is shown.

$^1$H-NMR spectrum (500 MHz, CDCl$_3$) δ ppm: 5.38(1H, dt, J=7.3, 4.0 Hz), 5.14(1H, s), 5.05(1H, t, J=9.3 Hz), 4.72(1H, s), 4.38(1H, dq, J=10.8, 6.3 Hz), 4.22 (1H, s), 3.98(1H, d, J=6.1 Hz), 3.06–3.16(4H, m), 2.82(1H, s), 2.49(1H, s), 2.28(1H, dd, J=11.6, 7.3 Hz), 2.21(1H, brt, J=12.5 Hz), 1.92–2.07(4H, m), 1.82(2H, m), 1.72(1H, m), 1.65(1H, m), 1.63(3H, s), 1.49(2H, m), 1.46(1H, m), 1.46 (3H, d, J=6.3 Hz), 1.37(1H, ddd, J=11.6, 11.6, 11.6 Hz), 1.20(2H.m), 1.18(3H, s), 1.07(1H, t, J=12.5 Hz), 0.99(3H, s), 0.96(3H, d, J=6.7 Hz), 0.95 (3H, d, J=6.4 Hz), 0.90(3H, d, J=7.3 Hz), 0.89(3H, t, J=7.3 Hz)

$^{13}$C-NMR spectrum (125 MHz, CDCl$_3$) δ ppm:
172.9(s), 172.8(s), 150.3(s), 142.8(s), 116.8(d), 111.0(t), 81.5(d), 77.5(d), 76.3(s), 76.1(d), 74.4(d), 74.3 (s), 53.2(d), 50.6(d), 49.4(d), 47.0(t), 45.7(t), 45.7(d), 44.2(t), 43.2(d), 42.2(s), 34.8(t), 31.0(t), 29.8(d), 29.5(d), 26.2(q), 23.9(q), 23.1(q), 21.6(q), 21.5(t), 21.1 (q), 20.4 (q), 19.4 (q), 11.2 (q)

Solubility: Readily soluble in an organic solvent such as methanol or dimethylsulfoxide and hardly soluble in water.
Distinction of acidic, neutral or basic substance:
Neutral substance
Color reaction: Sulfuric acid reaction positive,
Phosphorus molybdate reaction positive
$R_f$ value: 0.14 (using Kieselgel 60F$_{254}$, manufactured by Merck Co., developing solvent:
toluene/tetrahydrofuran/methanol (50:10:1))

Physicochemical characteristics of BE-49385F
Nature: White amorphous solid or crystals
Molecular formula: $C_{25}H_{38}O_5$
Mass spectrometry: [High resolution FAB-MS] as (M+H)$^+$:
measured value 419.2785, calculated value 419.2797

Ultraviolet absorption spectrum: Terminal absorption is shown.

$^1$H-NMR spectrum (500 MHz, CDCl$_3$) δ ppm:
5.13(1H, s), 5.03(1H, brt, J=9.2 Hz), 4.69(1H, s), 4.35 (2H, m), 4.23(1H, s), 3.24(1H, brs), 3.11(2H, m), 2.19(1H, dt, J=12.2, 2.4 Hz), 2.00–2.09(3H, m), 1.95(2 H, m), 1.83 (1H, dt, J=12.5, 3.0 Hz), 1.66(1H, m), 1.6 2(3H, s), 1.50(1H, dt, J=10.4, 4.0 Hz), 1.45(3H, d, J=6.4 Hz), 1.34(1H, ddd, J=12.5, 12.5, 12.5 Hz), 1.23(1H, dd, J=11.3, 8.8 Hz), 1.08 (1H, t, J=12.2 Hz), 1.00(3H, d, J=6.4 Hz), 0.96(3H, d, J=6.4 Hz), 0.93(3H.s)

$^{13}$C-NMR spectrum (125 MHz, CDCl$_3$) δ ppm:
173.1 (s), 150.6(s), 143.1(s), 116.6(d), 110.8(t), 77.5(d), 77.3(d), 76.4(s), 74.5(d), 57.6(d), 50.7(d), 50.2 (t), 49.5(d), 45.9(t), 45.8(d), 43.3(d), 42.3(s), 35.1(t), 29.8(d), 26.2(q), 24.1(q), 21.8(q), 21.5(t), 20.5(q), 19.4(q)

Solubility: Readily soluble in an organic solvent such as methanol or dimethylsulfoxide and hardly soluble in water.

Distinction of acidic, neutral or basic substance:

Neutral substance

Color reaction: Sulfuric acid reaction positive,
Phosphorus molybdate reaction positive R$_f$ value: 0.09 (using Kieselgel 60F$_{254}$, manufactured by Merck Co., developing solvent:
toluene/tetrahydrofuran/methanol (50:10:1))

Physicochemical characteristics of BE-49385G

Nature: White amorphous solid or crystals

Molecular formula: C$_{34}$H$_{549}$

Mass spectrometry: [High resolution FAB-MS] as (M–H)$^-$:

measured value 589.3730, calculated value 589.3741

Ultraviolet absorption spectrum: Terminal absorption is shown.

$^1$H-NMR spectrum (500 MHz, CDCl$_3$) δ ppm:
5.35(1H, dt, J=7.6, 3.7 Hz), 5.14(1H, s), 5.04(1H, brt, J=9.2 Hz), 4.71(1H, s), 4.38(1H, dq, J=11.0, 6.4H z), 4.22 (2H, m), 4.05(1H, brs), 3.82(1H, m), 3.02–3.16 (3H, m), 2.83(1H, s), 2.28(1H, dd, J=12.0, 7.6 Hz), 2.19(1H, brt, J=12.5 Hz), 2.05(2H, m), 1.96(2H, m), 1.81 (2H, m), 1.72 (1H, m), 1.63(3H, s), 1.54–1.64(2H, m), 1.46(3H, d, J=6.4 Hz), 1.13–1.40(7H, m), 1.09(1H, t, J=12.5 Hz), 0.98(3H, s), 0.95(3H, d, J=6.4 Hz), 0.90(3H, d, J=6.4 Hz), 0.88(3H, d, J=6.7 Hz), 0.88(3H, t, J=7.3H z)

$^3$C-NMR spectrum (125 MHz, CDCl$_3$) δ ppm:
173.2(s), 173.0(s), 150.4(s), 142.9(s), 116.7(d), 110.9(t), 81.5(d), 77.5(d), 76.4(s), 74.5(d), 73.0(d), 72.9 (d), 53.3(d), 50.5(d), 49.4(d), 47.2(t), 45.7(d), 45.7(t), 43.3(d), 42.3(s), 34.9(t), 34.2(d), 32.4(t), 31.3(t), 29.5(d), 29.3(t), 26.3(q), 23.9(q), 21.6(q), 21.5(t), 20.5(q), 19.4(q), 19.0(q), 11.2(q)

Solubility: Readily soluble in an organic solvent such as methanol or dimethylsulfoxide and hardly soluble in water.

Distinction of acidic, neutral or basic substance:

Neutral substance

Color reaction: Sulfuric acid reaction positive,
Phosphorus molybdate reaction positive R$_f$ value: 0.16 (using Kieselgel 60F$_{254}$, manufactured by Merck Co., developing solvent:
toluene/tetrahydrofuran/methanol (50:10:1))

Physicochemical characteristics of BE-49385H

Nature: White amorphous solid or crystals

Molecular formula: C$_3$ H$_{56}$O$_8$

Mass spectrometry: [High resolution FAB-MS] as (M+H)$^+$:

measured value 605.4050, calculated value 605.4054

Ultraviolet absorption spectrum: Terminal absorption is shown.

$^1$H-NMR spectrum (500 MHz, CDCl$_3$) δ ppm:
5.35(1H, dt, J=7.4, 3.4 Hz), 5.14(1H, s), 5.04(1H, brt, J=9.2 Hz), 4.71(1H, s), 4.38(1H, dq, J=11.0, 6.4H z), 4.21 (2H, m), 3.52(1H, m), 3.04–3.16(3H, m), 2.99 (1H, brd, J=3.7 Hz), 2.78(1H, s), 2.27(1H, dd, J=12.0, 7.0 Hz), 2.20 (1H, brt, J=12.5 Hz), 2.05(2H, m), 1.95(2H, m), 1.81(3H, m), 1.73(1H, m), 1.63(3H, brs), 1.46(3H, d, J=6.4 Hz), 1.33–1.50(4H, m), 1.22(1H, dd, J=12.0, 8.0 Hz), 1.00–1.12 (3H, m), 1.00(3H, d, J=6.7 Hz), 0.98(3H, s), 0.95(3H, d, J=6.4 Hz), 0.90(3H, d, J=6.4 Hz), 0.89 (3H, d, J=6.4 Hz), 0.87(3H, t, J=7.3 Hz)

$^{13}$C-NMR spectrum (125 MHz, CDCl$_3$) δ ppm:
173.6(s), 172.9(s), 150.4(s), 142.9(s), 116.7(d), 110.9(t), 81.5(d), 77.5(d), 76.4(s), 76.4(d), 74.5(d), 71.3 (d), 53.2(d), 50.5(d), 49.4(d), 47.0(t), 45.7(d), 45.6(t), 43.3(d), 42.3(s), 40.3(t), 34.9(t), 33.6(d), 31.3(d), 29.5(d), 28.0(t), 26.2(q), 23.9(q), 21.6(q), 21.5(t), 20.5 (q), 20.0(q), 19.4(q), 15.3(q), 10.7(q)

Solubility: Readily soluble in an organic solvent such as methanol or dimethylsulfoxide and hardly soluble in water.

Distinction of acidic, neutral or basic substance:

Neutral substance

Color reaction: Sulfuric acid reaction positive,
Phosphorus molybdate reaction positive R$_f$ value: 0.21 (using Kieselgel 60F$_{54}$, manufactured by Merck Co., developing solvent:
toluene/tetrahydrofuran/methanol (50:10:1))

Physicochemical characteristics of BE-49385A-Ac

Nature: White amorphous solid or crystals

Molecular formula: C$_{36}$H$_{56}$O$_8$

Mass spectrometry: [High resolution FAB-MS] as (M+H)$^+$: 617

$^1$H-NMR spectrum (500 MHz, CDCl$_3$) δ ppm:
5.44(1H, s), 5.29(1H, m), 5.17(1H, brs), 5.05(1H, t, J=8.4 Hz), 4.86(1H, brs), 4.35(1H, m), 3.57(1H, brs), 3.13(1H, dd, J=14.6, 9.8 Hz), 3.03(1H, m), 2.68(1H, br s), 2.49(1H, d, J=15.6 Hz), 2.39(1H, d, J=15.6 Hz), 2.2 6(1H, dd, J=12.0, 7.3 Hz), 2.20(3H, s), 2.19(1H, m), 1.93–2.11(4H, m), 1.66–1.80(3H, m), 1.63(3H, s), 1.50–1.56(2H, m), 1.46(3H, d, J=6.1 Hz), 1.30–1.43(3H, m), 1.23(3H, s), 1.12–1.24(2H, m), 1.07(1H, t, J=12.5 Hz), 0.98(3H, s), 0.94(3H, d, J=6.4 Hz), 0.93(3H, d, J=6.0 Hz), 0.90(3H, d, J=6.0 Hz), 0.87(3H, t, J=7.3 Hz)

$^{13}$C -NMR spectrum (125 MHz, CDCl$_3$) δ ppm:
172.7(s), 170.9(s), 167.2(s), 149.6(s), 143.0(s), 116.6(d), 111.9(t), 79.8(d), 76.5(d), 76.4(s), 74.3(d), 71.5 (s), 53.2(d), 50.5(d), 50.4(d), 48.2(t), 47.2(t), 45.7(t), 45.6(t), 45.5(d), 43.0(d), 42.2(s), 35.1(t), 31.0(t), 30.2(d), 29.6(d), 27.2(q), 26.2(q), 23.7(q), 21.7(q), 21.5 (t), 21.3(q), 20.6(q), 20.4(q); 19.4(q), 11.2(q)

Solubility: Readily soluble in an organic solvent such as methanol or dimethylsulfoxide and hardly soluble in water.

Distinction of acidic, neutral or basic substance:

Neutral substance

Color reaction: Sulfuric acid reaction positive,
Phosphorus molybdate reaction positive R$_f$ value: 0.6 (using Kieselgel 60F$_{254}$, manufactured by Merck Co., developing solvent: chloroform/methanol (20:1))

Biological activities (antifungal activities) of BE-49385

The minimum inhibitory concentrations of antifungal substances BE-49385 against various fungi were measured. The measurement of MIC was carried out by an agar dilution method using a culture medium prepared by mixing 900 ml of an agar solution containing 2.5 g of sterilized dipotassium hydrogenphosphate and 15 g of agar, with a solution obtained by dissolving 6.7 g of a yeast nitrogen base (manufactured by Difico Co.) and 10 g of glucose in 100 ml of purified water, followed by sterilization by means of sterilizing filter. BE-49385 was dissolved in dimethylsulfoxide to a concentration of 10 mg/ml and further diluted with dimethylsulfoxide to obtain a twice diluted series, and the dimethylsulfoxide concentration in the agar plate was adjusted to be 1%. On the prepared agar plate, 5 $\mu$l of the test strain solution adjusted to a concentration of $10^6$ cells per 1 ml, was dropped, followed by culturing at 28° C. for 3 days, whereupon the growth was evaluated.

The minimum inhibitory concentrations (MIC, unit: $\mu$ g/ml) of antifungal substance BE-49385A against various fungi, are shown in Table 1, and MICs of BE-49385 substances against Schizosaccharomyces pombe IAM4863 are shown in Table 2.

TABLE 1

Antifungal activities of BE-49385A

| Test strains | | MIC ($\mu$g/ml) |
|---|---|---|
| Kluyveromyces lactis | IFO 1267 | 0.78 |
| Saccharomyces cerevisiae | IFO 1267 | 3.13 |
| Candida albicans | IFO 1385 | 3.13 |
| Candida albicans | IFO 1270 | 0.78 |
| Penicillium chrysogenum | IFO 6223 | 0.39 |
| Aspergillus niger | IFO 31012 | 0.78 |

TABLE 2

Minimum inhibitory concentrations (MIC, $\mu$g/ml)
of BE-49385 against Schizosaccharomyces pombe IAM4863

| Compounds | MIC ($\mu$g/ml) |
|---|---|
| BE-49385A | <0.10 |
| BE-49385B | 0.39 |
| BE-49385C | 0.39 |
| BE-49385D | 0.78 |
| BE-49385E | 0.20 |
| BE-49385G | 0.39 |

As shown above, the antifungal substances BE-49385 exhibit remarkable growth inhibition activities against various fungi. Accordingly, the compounds of the present invention are useful as antifungal agents.

Now, a process for producing BE-49385 will be described.

The microorganism to be used for the production of the antifungal substances BE-49385 of the present invention, may be any microorganism so long as it is capable of producing the antifungal substances BE-49385. However, it is possible to use, for example, a microorganism F49385 strain having the following mycological characteristics, which was separated and collected anew from soil in Kamifurano-cho, Hokkaido, Japan, by the present inventors.
(1) Morphology Mycelia of F49385 strain are colorless with a smooth surface and have a width of from 0.8 to 2.4 $\mu$m. Conidiophores are formed infrequently with a length of from 5.6 to 6.4 $\mu$m and a width of the base portion being from 2.0 to 2.4 $\mu$m. Phialides may be formed directly on the mycelia or at the forward ends of conidiophores, and they are in a flask shape of 5.6 to 15.2×2.4 to 3.2 $\mu$m and have slender forward ends with a width of 0.8 $\mu$m. Conidia are formed in a chain form from the forward ends of the phialides and have a lemon shape of 2.8 to 4.8×2.4 to 2.8 $\mu$m with a smooth surface, with both ends being rectangular with a width of 0.4 $\mu$m
(2) Culture characteristics Table 3 shows the growth characteristics when F49385 strain was cultured at 25° C. for 10 days using various agar media. The colors in the Table were designated based on the names of colors in Methuen Handbook of color, 3rd ed., (1984).

TABLE 3

Growth characteristics of F49385 strain

| Culture media | Diameter of colony (mm) | Color of colony | Color of colony surface | State of colony |
|---|---|---|---|---|
| Czapek agar | 12 to 13 | White to soiled white | White | Flat and thin |
| Potato glucose agar | 19 to 20 | White to pale yellow white | Gray | Formation of velvet to powdery radial funis |
| Potato carrot agar | 22 to 24 | White to pale yellow white | Pale yellow white | Formation of cotton wool-like radial funis |

In each culture medium, the growth is relatively slow, and no secrete is observed on the colony surface. Further, the strain will not grow at 37° C. The growth temperature range of this strain is from 11 to 34° C., and the optimum growth temperature is 28° C. The growth pH range is from pH3.5 to pH9, and the optimum pH range is from pH4.5 to 6.5.

From the foregoing mycological characteristics, F49385 strain was identified as Paecilomyces inflatus (Burnside) Carmichael and named as Paecilomyces inflatus F49385 (Monophialidic species of Paecilomyces, p.13–15, Mycological Papers, No. 107, C.A.B. (1967), and Fungi Canadenses, No. 155, National Mycological Herbarium, Agriculture Canada (1979).

Further, this strain is deposited as an international deposition at National Institute of Bioscience and Human-Technology (NIBH), Agency of Industrial Science and Technology, Ministry of International Trade and Industry (address: 1–3, Higashi 1-chome, Tsukuba-shi, Ibaraki-ken 305, Japan), and the deposition number is FERM BP-5715 (date of original deposition: Nov. 8, 1995).

Mutants of Paecilomyces inflatus F49385 may be prepared by a conventional treating method for strain transformation such as treatment by irradiation with X-rays or ultraviolet rays, treatment with a mutagen such as nitrogen mustard, azaserine, nitrous acid, 2-aminopurine or N-methyl-N'-nitro-N-nitrosoguanidine (NTG), phage contact, transformation, transduction or conjugation.

For the production of BE-49385 substances of the present invention, a strain for producing BE-49385 is inoculated to a nutrient source-containing culture medium and aerobically grown to obtain a cultured product containing BE-49385 substances. As the nutrient sources, those known as nutrient sources for fungi can be used. For example, as a carbon source, commercially available glucose, glycerol, maltose, starch, sucrose, molasses or dextrin may be used alone or in combination as a mixture. As a nitrogen source, commercially available soybean powder, corn steep liquor, gluten meal, meet extract, yeast extract, dried yeast, cotton powder, peptone, wheat embryo, fish powder, meat meal, defatted rice bran, defatted meat and born powder, an inorganic ammonium salt or sodium nitrate may be used alone or in combination as a mixture. As an inorganic salt, commercially available calcium carbonate, sodium chloride, potassium chloride, magnesium sulfate, sodium bromide, sodium borate or various phosphoric acid salts may, for example, be used. Further, iron, manganese, zinc, cobalt or a heavy metal salt of e.g. molybdic acid may be added in a very small amount. In a case where foaming is vigorous, a vegetable oil such as soybean or linseed oil, a higher alcohol such as octadecanol, or various silicon compounds may, for example, be suitably added as a defoaming agent. Other substances may also be used so long as they are utilized by the producing strain and serve for the production of BE-49385, such as 3-(N-morpholino)propanesulfonic acid or sodium borate.

Culturing can be carried out in the same manner as a common method for producing a metabolite of a microorganism, and it may be solid culture or liquid culture. In the case of liquid culture, stationary culture, agitation culture, shaking culture or aerobic culture may be carried out. Particularly preferred is shaking culture or deep aerobic agitation culture. The culturing temperature is usually from 11 to 34 C., preferably from 25 to 30° C. A preferred pH of the culture medium is within a range of from 4.5 to 6.5, and the culturing time is usually from 48 to 500 hours, preferably from 120 to 400 hours. To collect the desired BE-49385 substances from the cultured product, a separation means which is commonly used for collecting a desired product from a metabolite produced by a microorganism, can suitably be used.

BE-49385 substances are present in the culture solution or in the cells and may be separated and purified from the culture solution or the cells by using common means for separation, such as a solvent extraction method, an ion exchange resin method, an adsorption or partition chromatography method and a gel filtration method alone or in proper combination.

As a preferred separation and purification example, the following method may be mentioned. Firstly, the culture solution is subjected to filtration to obtain the cells. The obtained cells are extracted with an organic solvent such as methanol or acetone. The obtained crude extract is subjected to partition by means of a water-ethyl acetate system or a water-n-hexane system, and the organic solvent layer is distilled to obtain a residue, which is then subjected to silica gel chromatography (eluted with n-hexane/ethyl acetate or with toluene/ethyl acetate), ODS chromatography (eluted with acetonitrile/water) or gel filtration chromatography (eluted with water-methanol system or ethanol), if necessary, repeatedly, to separate the respective BE-49385 substances and thus obtain them as amorphous solid or crystals.

To produce a compound wherein $R_2$ is an alkanoyl group among compounds of the general formula (I) of the present invention, an alkanoyl-modification method may be employed which is well known in the chemical field by using a compound of the general formula (II), i.e. BE-49385A, B, C, D, E, F, G or H, as the starting material. For example, such a compound can be easily prepared by reacting the starting material with a lower alkanoyl halide having from 2 to 6 carbon atoms or an anhydride of a lower aliphatic acid having from 1 to 6 carbon atoms at a low temperature or under heating, for example, at ordinary temperature, for a suitable period of time, if necessary in the presence of an alkali such as pyridine.

The antifungal composition of the present invention can be administered orally or parenterally in its clinical application, and it may be formulated to meet the administration mode by adding pharmacologically acceptable various additives,-as the case requires, and used as an antifungal agent.

The form for such formulation may, for example, be solid formulations such as tablets, capsules, granules, pills, troches, powders or suppositories, or liquid formulations such as syrups, elixirs, suspensions or injections, as well as aerosols, eyedrops, ointments, ophthalmic ointments, emulsions, creams, liniments or lotions. These formulations may be prepared in accordance with conventional methods commonly used in the field of drug formulations.

As the additives, various additives which are commonly used in the drug formulation field, can be used. For example, saccharides such as lactose or glucose, a starch such as corn, wheat or rice, a vegetable oil such as soybean oil, peanuts oil or sesame oil, a fatty acid such as stearic acid, an inorganic salt such as magnesium metasilicate aluminate or anhydrous calcium phosphate, a synthetic polymer such as polyvinylpyrrolidone or polyalkylene glycol, a fatty acid salt such as calcium stearate or magnesium stearate, an alcohol such as stearyl alcohol or benzyl alcohol, a synthetic cellulose derivative such as methyl cellulose, carboxymethyl cellulose, ethyl cellulose or hydroxy-propylmethyl cellulose, or others such as water, gelatin, talc and gum arabic, may, for example, be mentioned.

Further, in the case of a liquid formulation, it may be in such a form that at the-time of use, it is dissolved or suspended in water or in other suitable medium. Especially when administration is carried out by e.g. intramuscular injection, intravenous injection or subcutaneous injection, a suitable medium for such an injection may, for example, be distilled water for injection, a hydrochloric acid lidocaine aqueous solution (for intramuscular injection), physiological saline, an aqueous glucose solution, ethanol, liquid for intravenous injection (such as an aqueous solution of citric acid and sodium citrate) or an electrolyte solution (for intravenous drip and intravenous injection), or a mixed solution thereof. Further, a buffer or a preservative may be added.

These formulations may contain usually from 0.1 to 100 wt %, preferably from 5 to 100 wt %, of the active ingredient in the case of the above-mentioned solid formulations, and may contain from 0.1 to 10 wt %, preferably from 1 to 5 wt %, in the case of other formulations. Further, these formulations may contain other compounds which are therapeutically effective.

A practically preferred dose of the compound of the present invention varies depending upon the type of the compound used, the type of the composition blended, the sex, age, weight, diseased degree and the particular section to be treated of the patient, but it is usually from 0.1 to 100 mg/kg in the case of oral administration and from 0.01 to 100 mg/kg in-the case of parenteral administration, per adult per day. The number of times of administration varies depending upon the administration method and the symptom, but it is preferred to carry out the administration from one to five times per day.

BEST MODE FOR CARRYING OUT THE INVENTION

Now, the present invention will be described in further detail with reference to Examples, but the present invention is by no means thereby restricted.

EXAMPLE 1

Method for producing BE-49385

1–1) Method for preparing a fraction containing BE-49385C, a fraction containing BE-49385A and BE-49385B, and a fraction containing BE-49385D, E and BE-49385F Fungus F49385 strain inoculated to a slant soft agar plate, was inoculated to six Erlenmeyer flasks having a capacity of 500 ml containing 100 ml of a culture medium (pH 6) comprising 10% of glucose, 3.0% of maltose, 0.3% of yeast extract, 1.0% of wheat embryo, 0.5% of gluten meal, 0.3% of polypeptone, 0.1% of sodium nitrate, 0.2% of sodium chloride, 0.1% of dipotassium hydrogenphosphate, 0.05% of magnesium sulfate, 0.00008% of zinc sulfate, 0.002% of calcium chloride, 0.0002% of ferrous sulfate, 0.00004% of cuprous chloride, 0.00004% of manganese chloride, 0.00004% of cobalt chloride, 0.00008% of sodium borate and 0.00024% of ammonium molybdate, and cultured on a rotary shaker (180 rpm) at 28° C. for 96 hours. 200 ml of this culture solution was inoculated to each of three jar fermentators having a capacity of 20 lit. and containing 10 lit of the above culture medium, and cultured at 28° C. for 312 hours.

The culture solution (26.5 lit.) thus obtained was sterilized at 90° C. for 10 minutes, and then cells were separated by filtration. To the cells, methanol (20 lit.) was added, followed by stirring for a few hours. Then, the cells were filtered off to obtain a methanol extract solution. Acetone (10 lit.) was added to the cells after methanol extraction, followed by stirring for a few hours, whereupon the cells were filtered off to obtain an acetone extract solution. The methanol extract solution and the acetone extraction solution were put together and concentrated under reduced pressure to about 2 lit. To this concentrated solution, n-hexane (1 lit.) and ethyl acetate (1 lit.) were added for extraction. The obtained n-hexane/ethyl acetate extract solution was concentrated under reduced pressure, and to the residue, n-hexane (500 ml) was added, followed by filtration, and the filtrate was subjected to a chromatocolumn (4.0×25 cm) of silica gel (Wako Junyaku K.K.) to extract with a mixed solvent of n-hexane with a n-hexane/ethyl acetate (8:1 to 1:1). The extracted active fraction was concentrated and dried under reduced pressure to obtain 570 mg of a fraction Fr.1 containing BE-49385C, 1526 mg of a fraction Fr.2 containing BE-49385A and BE-49385B, and 908 mg of a fraction Fr.3-containing BE-49385D, E and BE-49385F.

1—1—1) Method for preparing a crude material containing BE-49385A and a crude material containing BE-49385B Fr.2 obtained in 1—1 was dissolved in methanol (5 ml), and subjected to a chromatocolumn (4.0×45 cm) of Sephadex LH-20 (manufactured by Pharmacia Co.). The desired fraction obtained by elution with 80% methanol, was concentrated under reduced pressure, and the concentrate was dissolved in ethanol (3 ml) and subjected to a chromatocolumn (4.0×45 cm) of Sephadex LH-20 (manufactured by Pharmacia Co.). Elution was carried out with ethanol, and the eluted active fraction was concentrated under reduced pressure, and the concentrate was dissolved in ethanol (6 ml) and subjected to a Develosil ODS-10 column (20×250 mm, manufactured by Nomura Kagaku K.K.) in an amount of 0.2 ml each time and then subjected to fractional high performance liquid chromatography using 85% acetonitrile as a mobile phase to obtain 508 mg of a crude substance Fr.2-1 containing BE-49385A and 25 mg of a crude substance Fr.2—2 containing BE-49385B.

1—1—1—1) Method for producing BE-49385A

Fr.2-1 obtained in 1—1—1 was dissolved in toluene (10 ml) and subjected to a chromatocolumn (2.5×33 cm) of silica gel (manufactured by Merck Co.), whereby elution was conducted with a mixed solvent of toluene/ethyl acetate (9:1 to 8:1). The desired fraction obtained by the elution was concentrated under reduced pressure, and the concentrate was further dissolved in ethanol (5 ml) and subjected to YMC pack ODS-A column (20×250 mm, manufactured by YMC Co.) in an amount of 0.3 ml each time and subjected to fractional high performance liquid chromatography using 88% acetonitrile as a mobile phase, whereupon the desired fraction was concentrated under reduced pressure. To this concentrated solution, water (50 ml) was added, and the mixture was acidified with 1N hydrochloric acid and then extracted with ethyl acetate (50 ml). The ethyl acetate extract solution was further washed with water (50 ml), and the ethyl acetate extract solution was concentrated to dryness to obtain 485 mg of a white powder of BE-49385A.

1—1—1-2) Method for producing BE-49385B Fr.2–2 obtained in 1—1—1 was dissolved in toluene (3 ml) and subjected to a chromatocolumn (2.5×33 cm) of silica gel (manufactured by Merck Co.), whereby elution was carried out with a mixed solvent of toluene/ethyl acetate (9:1 to 8:1). The desired fraction obtained by the elution was concentrated under reduced pressure, and the concentrate was further dissolved in ethanol (1 ml) and subjected to a YMC pack ODS-A column (20×250 mm, manufactured by YMC Co.) in an amount of 0.3 ml each time, and subjected to fractional high performance liquid chromatography using 90% acetonitrile as a mobile phase, whereupon the desired fraction was concentrated under reduced pressure. To this concentrated solution, water (50 ml) was added, and the mixture was acidified with 1N hydrochloric acid and then extracted with ethyl acetate (50 ml). The ethyl acetate extract solution was further washed with water (50 ml), and the ethyl acetate extract solution was concentrated to dryness to obtain 9.7 mg of a white powder of BE-49385B.

1—1-2) Method for producing BE-49385C

Fr.1 obtained in 1—1 was dissolved in methanol (3 ml) and subjected to a chromatocolumn (2.5X35 cm) of Sephadex LH-20 (manufactured by Pharmacia Co.). The desired fraction obtained by elution with 80% methanol, was concentrated under reduced pressure, and the concentrate was further dissolved in ethanol (3 ml) and subjected to a chromatocolumn (4.0×45 cm) of Sephadex of LH-20 ( manufactured by Pharmacia Co.), whereby elution was carried out with ethanol, and the eluted active fraction was concentrated under reduced pressure. The concentrate was dissolved in toluene (3 ml) and subjected to a chromatocolumn (2.5×33 cm) of silica gel (manufactured by Merck Co.), whereby elution was carried out with a mixed solvent of toluene/ethyl acetate (49:1 to 22:3). The desired fraction obtained by the elution was concentrated under reduced pressure, and the concentrate was further dissolved in ethanol (4 ml) and subjected to a Develosil ODS-10 column (20×250 mm, manufactured by Nomura Kagaku-K.K.) in an amount of 0.4 ml each time, and subjected to fractional high performance liquid chromatography using 92% acetonitrile as a mobile phase, to obtain 42 mg of a crude substance containing BE-49385C. This crude substance was dissolved in ethanol (4 ml) and subjected to a YMC pack ODS-A column (20×250 mm, manufactured by YMC Co.) in an amount of 0.4 ml each time and subjected to fractional high performance liquid chromatography using 95% acetonitrile as a mobile phase, whereby the desired fraction was concentrated under reduced pressure. To this concentrated solution, water (50 ml) was added, and the mixture was acidified with IN hydrochloric acid and then extracted with ethyl acetate (50 ml). The ethyl acetate extract solution was further washed with water (50 ml), and the ethyl acetate extract solution was concentrated to dryness to obtain 42.5 mg of a white powder of BE-49385C.

1—1-3) Method for preparing a fraction containing BE-49385D and BE-49385E and a fraction containing BE-49385F Fr.3 obtained in 1—1 was dissolved in methanol (5 ml) and subjected to a chromatocolumn (4.0×45 cm) of Sephadex LH-20 (manufactured by Pharmacia Co.). The desired fraction obtained by elution with 80% methanol was concentrated under reduced pressure, and the concentrate was further dissolved in ethanol (3 ml) and subjected to a chromatocolumn (4.0×45 cm) of Sephadex LH-20 (manufactured by Pharmacia Co.), whereby elution was carried out with ethanol, and the eluted active fraction was concentrated under reduced pressure. The concentrate was dissolved in a mixed solvent of toluene/ethyl acetate (4:1, 10 ml) and subjected to a chromatocolumn (2.0×15 cm) of silica gel (manufactured by Merck Co.), whereby elution was carried out with a mixed solvent of toluene/ethyl acetate (4:1 to 11:9), and the active fraction was concentrated to dryness, to obtain 53 mg of a fraction Fr.3–1 containing BE-49385D and BE-49385E and 46 mg of a fraction Fr.3-2 containing BE-49385F.

1—1-3-1) Method for preparing a crude substance containing BE-49385D and a crude substance containing BE-49385E Fr.3-1 obtained in 1—1-3 was dissolved in ethanol (3 ml) and subjected to a Develosil ODS-10 column (20×250 mm, manufactured by Nomura Kagaku K.K.) in an amount of 0.3 ml each time and subjected to fractional high performance liquid chromatography using 70% acetonitrile as a mobile phase, and the active fraction was concentrated to dryness to obtain 5.1 mg of a crude substance Fr.3-1—1 containing BE-49385D and 25 mg of a crude substance Fr.3-1-2 containing BE-49385E.

1—1-3-1—1) Method for producing BE-49385D

Fr.3–1–1 obtained in 1–1–3–1 was dissolved in ethanol (1 ml) and subjected to a YMC pack ODS-A column (20×250 mm, manufactured by YMC Co.) in an amount of 0.3 ml each time and subjected to fractional high performance liquid chromatography using 70% acetonitrile as a mobile phase and the desired fraction was concentrated under reduced pressure. To this concentrated solution, water (50 ml) was added, and the mixture was acidified with 1N hydrochloric acid and then extracted with ethyl acetate (50 ml). The ethyl acetate extract solution was further washed with water (50 ml), and the ethyl acetate solution was concentrated to dryness to obtain 3.6 mg of a white powder of BE-49385D.

1—1-3-1-2) Method for producing BE-49385E

Fr.3-1-2 obtained in 1—1-3-1 was dissolved in ethanol (1.5 ml) and subjected to a YMC pack ODS-A column (20×250 mm, manufactured by YMC Co.) in an amount of 0.2 ml each time, and subjected to fractional high performance liquid chromatography using 70% acetonitrile as a mobile phase, and the desired fraction was concentrated under reduced pressure. To this concentrated solution, water (50 ml) was added, and the mixture was acidified with 1N hydrochloric acid. Then, it was extracted with ethyl acetate (50 ml), and the ethyl acetate extract solution was further washed with water (50 ml), and the ethyl acetate extract solution was concentrated to dryness to obtain 20.5 ml of a white powder of BE-49385E.

1—1-3-2) Method for producing BE-49385F

Fr.3-2 obtained in 1—1-3 was dissolved in ethanol (4 ml) and subjected to a Develosil ODS-10 column (20×250 mm, manufactured by Nomura Kagaku K.K.) in an amount of 0.3 ml each time, and subjected to fractional high performance liquid chromatography using 55% acetonitrile as a mobile phase. The active fraction was concentrated to dryness to obtain 28 mg of a crude substance containing BE-49385F. The crude substance was dissolved in ethanol (2.5 ml) and subjected to a YMC pack ODS-A column (20×250 mm, manufactured by YMC Co.) in an amount of 0.3 ml each time, and subjected to fractional high performance liquid chromatography using 57% acetonitrile as a mobile phase. The desired fraction was concentrated under reduced pressure. To this concentrated solution, water (50 ml) was added, and the mixture was acidified with 1N hydrochloric acid, and then extracted with ethyl acetate. The ethyl acetate extract solution was further washed with water (50 ml). The ethyl acetate extract solution was concentrated to dryness to obtain 32.1 mg of a white powder of BE-49385F.

1-2) Method for preparing a fraction containing BE-49385G and BE-49385H

Fungus F49385 strain inoculated on a slant soft agar plate, was inoculated to two Erlenmeyer flasks having a capacity of 500 ml and containing 100 ml of a culture medium (pH 6) comprising 1.0% of glucose, 3.0% of maltose, 0.3% of yeast extract, 1.0% of wheat embryo, 0.5% of gluten meal, 0.3% of polypeptone, 0.1% of sodium nitrate, 0.2% of sodium chloride, 0.1% of dipotassium hydrogenphosphate, 0.05% of magnesium sulfate, 0.00008% of zinc sulfate, 0.002% of calcium chloride, 0.0002% of ferrous sulfate, 0.00004% of cuprous chloride, 0.00004% of manganese chloride, 0.00004% of cobalt chloride, 0.00008% of sodium borate and 0.00024% of ammonium molybdate, and cultured on a rotary shaker (180 rpm) at 28° C. for 96 hours. 200 ml of this culture solution was inoculated to one jar fermentator having a capacity of 20 lit. and containing 10 lit. of the above culture medium and cultured at 28° C. for 96 hours. 2 lit. of this culture solution was inoculated to one jar fermentator having a capacity of 200 lit. and containing 100 lit. of the above culture medium, and cultured at 28° C. for 336 hours.

The culture solution (100 lit.) thus obtained was sterilized at 90° C. for 10 minutes, followed by filtration to separate the cells, and methanol (60 lit.) was added to the cells, followed by stirring for a few hours. Then, the cells were filtered off to obtain a methanol extract solution. This methanol extract solution was concentrated under reduced pressure to about 2 lit., and n-hexane (3 lit.) and ethyl acetate (3 lit.) were added to this concentrated solution for extraction. To the lower layer after the n-hexane/ethyl acetate extraction, ethyl acetate (5 lit.) was added for extraction. This extract solution was combined with the n-hexane/ethyl acetate extract solution, followed by concentration under reduced pressure. To the residue obtained by concentration, n-hexane (200 ml) and toluene (200 ml) were added, followed by filtration. The filtrate was subjected to a chromatocolumn (4.0×50 cm) of silica gel (manufactured by Wako Junyaku K.K.) and the eluted with toluene and a mixed solvent of toluene/ethyl acetate (19:1 to 1:1). The extracted active fraction was concentrated to dryness under reduced pressure to obtain 3.48 g of a fraction Fr.4 containing BE-49385G and BE-49385H.

1-2-1) Method for preparing a crude substance containing BE-49385G and a crude substance containing BE-49385H Fr.4 obtained in 1-2 was dissolved in ethanol (3 ml) and subjected to a chromatocolumn (3.0×45 cm) of Sephadex LH-20 (manufactured by Pharmacia Co.). The desired fraction obtained by elution with ethanol was concentrated under reduced pressure. The concentrate was dissolved in toluene (30 ml) and subjected to a chromatocolumn (2.0×30 cm) of silica gel (manufactured by Merck Co.) and eluted with a mixed solvent of toluene/ethyl acetate (19:6 to 33:17). The obtained active fraction was concentrated under reduced pressure, and the concentrate was further dissolved in ethanol (2 ml) and subjected to a chromatocolumn (3.0×45 cm) of Sephadex LH-20 (manufactured by Pharmacia Co.), whereby elution was carried out with ethanol, and the eluted active fraction was concentrated under reduced pressure. The concentrate was dissolved in ethanol (5 ml) and subjected to a Develosil ODS-10/20 column (50×500 mm, manufactured by Nomura Kagaku K.K.) and subjected to fractional high performance liquid chromatography using 70% acetonitrile as a mobile phase. The active fraction was concentrated to dryness to obtain 10 mg of a crude substance Fr.4–1 containing BE-49385G and 10 mg of a crude substance Fr.4–2 containing BE-49385H.

1-2-1—1) Method for producing BE-49385G

Fr.4–1 obtained in 1-2-1 was dissolved in ethanol (0.9 ml) and subjected to a YMC pack ODS-AS-10 column (20×250 mm, manufactured by YMC Co.) in an amount of 0.3 ml each time, and subjected to fractional high performance chromatography using 70% acetonitrile as a mobile phase. The desired fraction was concentrated under reduced pressure. This concentrated solution was dissolved in ethanol (1.5 ml) and subjected to a YMC pack ODS-AS-5 column (20×250 mm, manufactured by YMC Co.) in an amount of 0.5 ml each time and subjected to fractional high performance liquid chromatography using 68% acetonitrile as a mobile phase. The desired fraction was concentrated under reduced pressure. This concentrated solution was dissolved in ethanol (0.6 ml) and subjected to a YMC pack ODS-AS-5 column (20×250 mm, manufactured by YMC Co.) and subjected to fractional high performance liquid chromatography using 65% acetonitrile as a mobile phase. The desired fraction was concentrated under reduced pressure. This concentrated solution was dissolved in ethanol (0.4 ml) and subjected to a YMC pack ODS-AS-10 column (20×250 mm, manufactured by YMC Co.) and subjected to fractional high performance liquid chromatography using 70% acetonitrile as a mobile phase. The desired fraction was concentrated under reduced pressure. To the concentrated solution, water (30 ml) was added, and the mixture was acidified with 1N hydrochloric acid and then extracted with ethyl acetate (30 ml) The ethyl acetate extract solution was further washed with water (30 ml), and the ethyl acetate extract solution was concentrated to dryness to obtain 3.9 mg of a white powder of BE-49385G.

1-2—1-2) Method for producing BE-49385H

Fr.4–2 obtained in 1–2–1 was dissolved in ethanol (1.5 ml) and subjected to a YMC pack ODS-AS-5 column (20×250 mm, manufactured by YMC Co.) in an amount of 0.5 ml each time, and subjected to fractional high performance liquid chromatography using 75% acetonitrile as a mobile phase. The desired fraction was concentrated under reduced pressure. This concentrated solution was dissolved in ethanol (0.8 ml) and subjected to a YMC pack ODS-AS-5 column (20×250 mm, manufactured by YMC Co.) in an amount of 0.4 ml each time, and subjected to fractional high performance liquid chromatography using 72% acetonitrile as a mobile phase. The desired fraction was concentrated under reduced pressure. To the concentrated solution, water (20 ml) was added, and the mixture was acidified with IN hydrochloric acid and then extracted with ethyl acetate (20 ml). The ethyl acetate extract solution was further washed with water (20 ml), and the ethyl acetate extract solution was concentrated to dryness to obtain 1.4 mg of a white powder of BE-49385H.

EXAMPLE 2

Method for producing BE-49385A-Ac 1.0 mg of BE-49385A was dissolved in 0.25 ml of anhydrous pyridine, and 0.25 ml of acetic anhydride was added thereto, followed by stirring at room temperature for 4 hours. The reaction mixture was concentrated under reduced pressure, and water was added thereto, followed by concentration under reduced pressure to dryness. This operation was repeated to obtain BE-49385A-Ac.

Formulation Examples of the compounds of the present invention will be shown below, but formulations of the compounds of the present invention are not limited to such Formulation Examples.

FORMULATION EXAMPLE 1

10 Parts of BE-49385A, 15 parts of heavy magnesium oxide and 75 parts of lactose were uniformly mixed to obtain a powdery or fine granular powder having a particle size of at most 350 $\mu$m. This powder was put into a capsule container to obtain a capsule drug.

FORMULATION EXAMPLE 2

45 Parts of BE-49385A, 15-parts of starch, 16 parts of lactose, 21 parts of crystalline cellulose, 3 parts of polyvinyl alcohol and 30 parts of distilled water were uniformly mixed, then pulverized, granulated and dried and then sieved to obtain granules having a size with a diameter of from 1410 to 177 $\mu$m.

FORMULATION EXAMPLE 3

Granules were prepared in the same manner as in Formulation Example 2, and then 3 parts of calcium stearate was added to 96 parts of the granules, followed by compression molding to obtain tablets having a diameter of 10 mm.

FORMULATION EXAMPLE 4

10 Parts of crystalline cellulose and 3 parts of calcium stearate were added to 90 parts of the granules obtained by the method of Formulation Example 2, followed by compression molding to obtain tablets having a diameter of 8 mm. Then, a mixed suspension of syrup gelatin and precipitated calcium carbonate, was added thereto to obtain sugar-coated tablets.

FORMULATION EXAMPLE 5

1 Part of BE-49385A, 49.5 parts of Macrogol 4000 and 49.5 parts of Macrogol 400 were mixed and well kneaded to be homogeneous, thereby to obtain a n ointment.

INDUSTRIAL APPLICABILITY

BE-49385 substances of the present invention have antifungal activities and thus are useful as antifungal agents.

We claim:

1. A compound represented by the general formula (I):

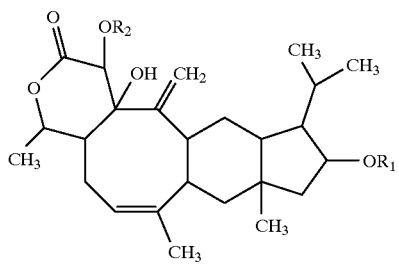
(I)

wherein $R_1$ is a hydrogen atom, or

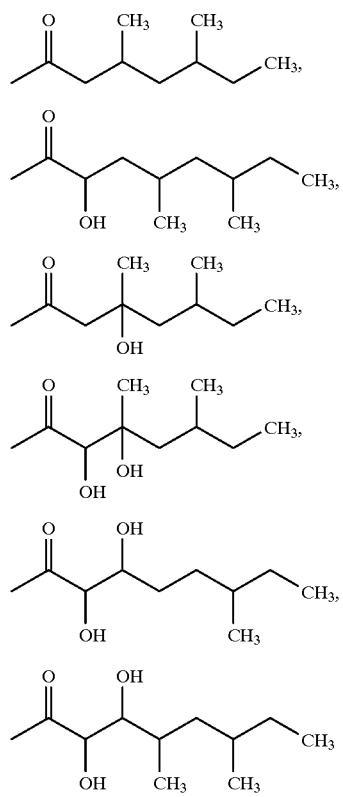

or

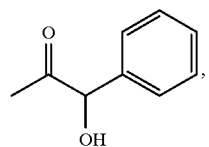

and $R_2$ is a hydrogen atom or a lower alkanoyl group.

2. A process for producing a compound represented by the general formula (I):

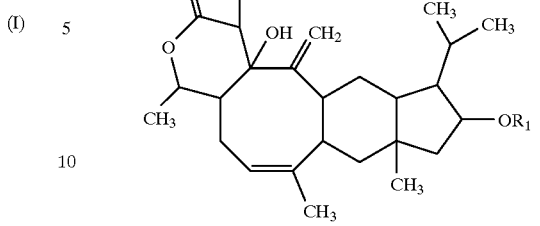
(I)

wherein $R_2$ is a hydrogen atom or a lower alkanoyl group, and $R_1$ is as defined below, which comprises culturing a microorganism strain F49385 deposited under the accession number FERM BP-5715 and producing a compound represented by the general formula (II):

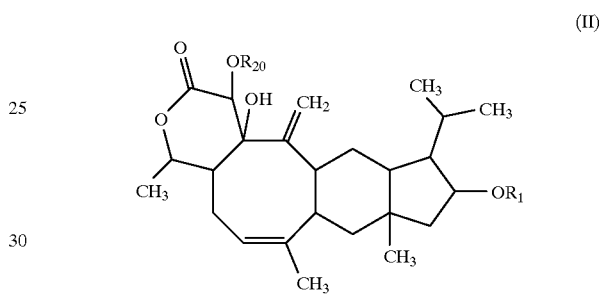
(II)

wherein $R_1$ is a hydrogen atom, or

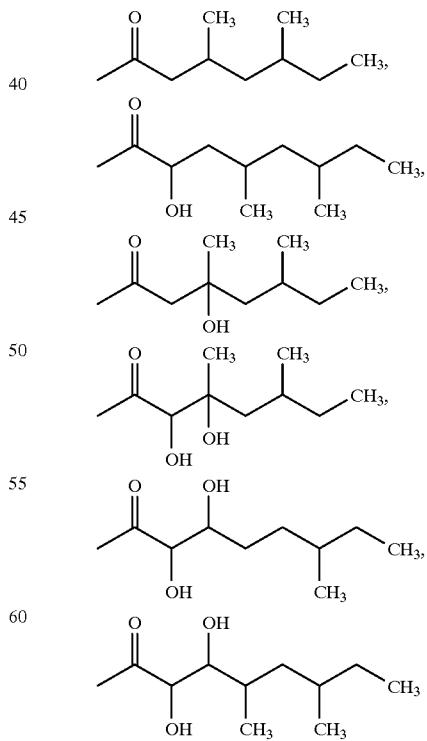

or

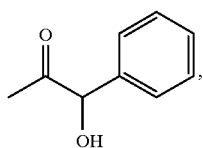

and $R_{20}$ is a hydrogen atom, collecting the compound represented by the general formula (II), and, optionally, converting it to a compound wherein $R_2$ is a lower alkanoyl group.

3. An antifungal agent containing a compound represented by the general formula (I):

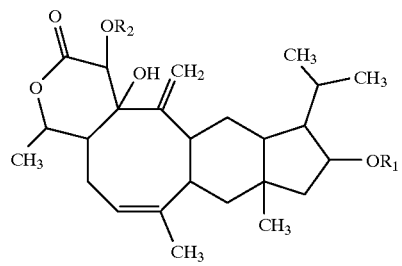

wherein $R_1$ is a hydrogen atom, or

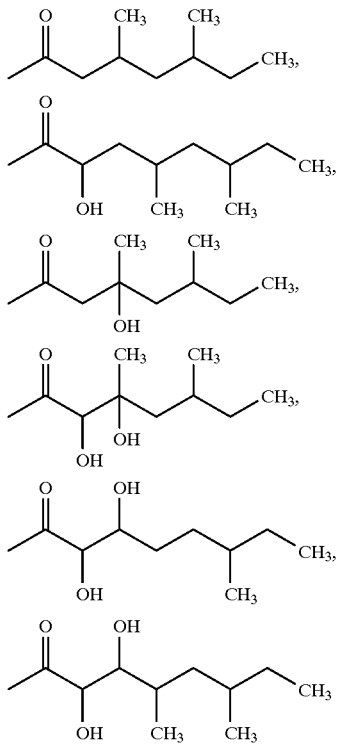

or

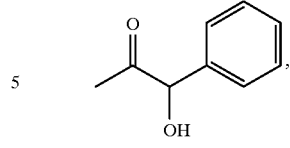

and $R_2$ is a hydrogen atom or a lower alkanoyl group, as an active ingredient and a pharmacologically acceptable additive.

4. A microorganism strain F49385 deposited under the accession number FERM BP-5715, which produces the compound represented by the general formula (II):

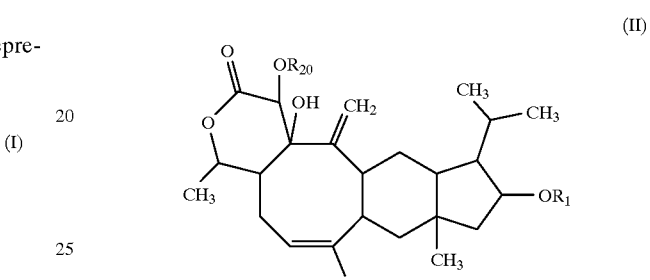

wherein $R_1$ is a hydrogen atom, or

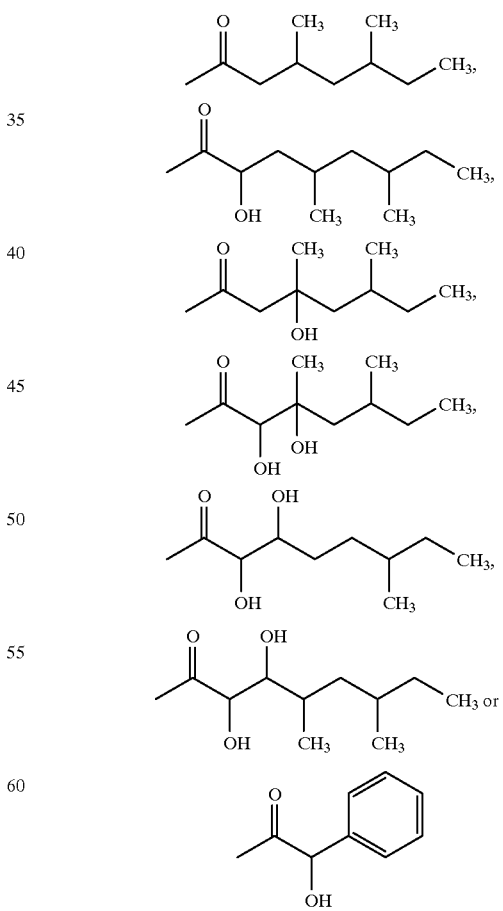

and $R_{20}$ is a hydrogen atom.

5. The compound of claim 1, wherein $R_1$ is

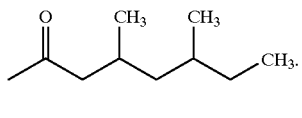

6. The compound of claim 1, wherein $R_1$ is

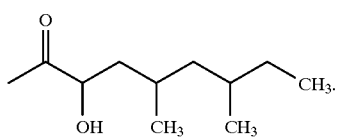

7. The compound of claim 1, wherein $R_1$ is

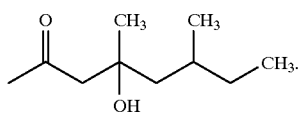

8. The compound of claim 1, wherein $R_1$ is

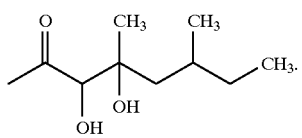

9. The compound of claim 1, wherein $R_1$ is

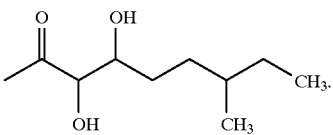

10. The compound of claim 1, wherein $R_1$ is

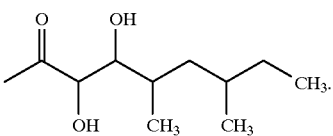

11. The compound of claim 1, wherein $R_1$ is

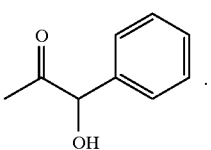

12. The compound of claim 1, wherein $R_1$ is a hydrogen atom.

13. The compound of claim 1, wherein $R_2$ is a hydrogen atom.

14. The compound of claim 1, wherein $R_2$ is a lower alkyanoyl group.

15. The compound of claim 14, wherein said lower alkyanoyl group is a $C_{1-6}$ linear or branched alkanoyl group.

* * * * *